United States Patent
Haugen et al.

(10) Patent No.: US 9,179,892 B2
(45) Date of Patent: Nov. 10, 2015

(54) SYSTEM AND METHOD FOR ULTRASOUND IMAGING

(75) Inventors: Geir Ultveit Haugen, Oslo (NO); Kjell Kristoffersen, Horten (NO)

(73) Assignee: General Electric Company, Wauwatosa, WI (US)

(*) Notice: Subject to any disclaimer, the term of this patent is extended or adjusted under 35 U.S.C. 154(b) by 751 days.

(21) Appl. No.: 12/941,367

(22) Filed: Nov. 8, 2010

(65) Prior Publication Data
US 2012/0116224 A1 May 10, 2012

(51) Int. Cl.
*A61B 8/00* (2006.01)
*A61B 8/08* (2006.01)
*A61B 8/14* (2006.01)

(52) U.S. Cl.
CPC .............. *A61B 8/483* (2013.01); *A61B 8/0883* (2013.01); *A61B 8/145* (2013.01)

(58) Field of Classification Search
USPC .................................................. 600/437–472
See application file for complete search history.

(56) References Cited

U.S. PATENT DOCUMENTS

| | | | | |
|---|---|---|---|---|
| 5,090,413 A * | 2/1992 | Yoshioka | | 600/443 |
| 5,235,986 A * | 8/1993 | Maslak et al. | | 600/447 |
| 5,454,371 A | 10/1995 | Fenster et al. | | |
| 5,497,776 A * | 3/1996 | Yamazaki et al. | | 600/445 |
| 5,720,291 A * | 2/1998 | Schwartz | | 600/456 |
| 5,855,556 A * | 1/1999 | Shirai | | 600/440 |
| 5,860,924 A | 1/1999 | Quistgaard | | |
| 5,882,306 A * | 3/1999 | Ramamurthy et al. | | 600/440 |
| 5,904,652 A * | 5/1999 | Gilbert et al. | | 600/447 |
| 5,993,390 A * | 11/1999 | Savord et al. | | 600/437 |
| 6,050,944 A * | 4/2000 | Holley et al. | | 600/441 |
| 6,174,287 B1 * | 1/2001 | Resnick et al. | | 600/458 |
| 6,234,968 B1 * | 5/2001 | Sumanaweera et al. | | 600/443 |
| 6,245,017 B1 * | 6/2001 | Hashimoto et al. | | 600/447 |
| 6,374,674 B1 * | 4/2002 | Mine | | 73/606 |
| 6,419,633 B1 * | 7/2002 | Robinson et al. | | 600/443 |
| 6,464,642 B1 * | 10/2002 | Kawagishi | | 600/454 |
| 6,480,732 B1 | 11/2002 | Tanaka et al. | | |
| 6,544,175 B1 * | 4/2003 | Newman | | 600/437 |
| 6,582,367 B1 * | 6/2003 | Robinson et al. | | 600/443 |
| 6,719,697 B2 * | 4/2004 | Li | | 600/454 |

(Continued)

FOREIGN PATENT DOCUMENTS

| | | |
|---|---|---|
| CN | 1805711 A | 7/2006 |
| CN | 101080202 A | 11/2007 |

(Continued)

OTHER PUBLICATIONS

Unofficial translation of Chinese Search Report from corresponding CN Application No. 201110365515.8 dated Jun. 4, 2014.

(Continued)

*Primary Examiner* — James Kish

(57) ABSTRACT

A system and method for ultrasound imaging includes acquiring volumetric data of a volume of interest with an ultrasound imaging system. The system and method includes acquiring planar data with the ultrasound imaging system during the process of acquiring the volumetric data, the planar data including data of a plane through the volume of interest. The system and method includes displaying a reference image based on the planar data during the process of acquiring the volumetric data. The system and method also includes displaying an image based on the volumetric data.

12 Claims, 4 Drawing Sheets

(56) References Cited

U.S. PATENT DOCUMENTS

| | | | |
|---|---|---|---|
| 7,131,947 B2* | 11/2006 | Demers | 600/447 |
| 7,270,634 B2* | 9/2007 | Scampini et al. | 600/447 |
| 7,331,927 B2* | 2/2008 | Steen | 600/447 |
| 7,645,237 B2* | 1/2010 | Frisa et al. | 600/447 |
| 7,881,774 B2* | 2/2011 | Kobayashi | 600/428 |
| 7,894,649 B2* | 2/2011 | Fu et al. | 382/128 |
| 8,012,090 B2* | 9/2011 | Steen | 600/437 |
| 8,233,681 B2* | 7/2012 | Aylward et al. | 382/128 |
| 8,376,949 B2* | 2/2013 | Sasaki et al. | 600/443 |
| 8,403,854 B2* | 3/2013 | Sasaki | 600/443 |
| 8,622,913 B2* | 1/2014 | Dentinger et al. | 600/456 |
| 2004/0158154 A1 | 8/2004 | Hanafy et al. | |
| 2004/0215077 A1* | 10/2004 | Witt et al. | 600/443 |
| 2005/0090745 A1* | 4/2005 | Steen | 600/447 |
| 2005/0096538 A1* | 5/2005 | Chomas et al. | 600/437 |
| 2005/0228280 A1* | 10/2005 | Ustuner et al. | 600/443 |
| 2005/0283075 A1 | 12/2005 | Ma et al. | |
| 2005/0283078 A1* | 12/2005 | Steen | 600/447 |
| 2006/0004291 A1* | 1/2006 | Heimdal et al. | 600/459 |
| 2006/0020204 A1 | 1/2006 | Serra et al. | |
| 2007/0014446 A1 | 1/2007 | Sumanaweera et al. | |
| 2007/0078344 A1* | 4/2007 | Rafter | 600/450 |
| 2007/0167769 A1* | 7/2007 | Ikuma et al. | 600/437 |
| 2007/0167801 A1* | 7/2007 | Webler et al. | 600/459 |
| 2008/0129732 A1* | 6/2008 | Johnson et al. | 345/424 |
| 2009/0018448 A1* | 1/2009 | Seo et al. | 600/443 |
| 2009/0030313 A1* | 1/2009 | Prater et al. | 600/443 |
| 2009/0054776 A1* | 2/2009 | Sasaki | 600/443 |
| 2009/0149756 A1* | 6/2009 | Soler et al. | 600/443 |
| 2009/0171208 A1* | 7/2009 | Osumi et al. | 600/443 |
| 2010/0036247 A1 | 2/2010 | Yamamoto et al. | |
| 2010/0174194 A1* | 7/2010 | Chiang et al. | 600/447 |
| 2011/0172526 A1* | 7/2011 | Lachaine et al. | 600/439 |
| 2011/0301463 A1* | 12/2011 | Fujii et al. | 600/443 |
| 2011/0306886 A1 | 12/2011 | Daft et al. | |
| 2012/0095343 A1* | 4/2012 | Smith et al. | 600/447 |
| 2012/0245465 A1 | 9/2012 | Hansegard et al. | |
| 2013/0021336 A1 | 1/2013 | Tsukagoshi et al. | |
| 2015/0065877 A1 | 3/2015 | Orderud | |

FOREIGN PATENT DOCUMENTS

| | | |
|---|---|---|
| EP | 1609424 A1 | 12/2005 |
| JP | 201276066 A | 10/2001 |
| WO | 2008044173 A1 | 4/2008 |
| WO | 2011/016037 A1 | 2/2011 |

OTHER PUBLICATIONS

International Search Report and Written Opinion regarding International Application No. PCT/US2014/048555, mail date Apr. 21, 2015, 17 pages.

Invitation to Pay Additional Fees and, Where Applicable, Protest Fee regarding International Application No. PCT/US2014/048555, mail date Jan. 22, 2015, 5 pages.

* cited by examiner

SYSTEM AND METHOD FOR ULTRASOUND IMAGING

FIELD OF THE INVENTION

This disclosure relates generally to a system and method for ultrasound imaging. The system and method includes displaying a reference image based on planar data during the process of acquiring volumetric data.

BACKGROUND OF THE INVENTION

A conventional ultrasound imaging system comprises an array of ultrasonic transducer elements for transmitting an ultrasound beam and receiving a reflected beam from an object being studied. By selecting the time delay (or phase) and amplitude of the applied voltages, the individual transducer elements can be controlled to produce ultrasonic waves which combine to form a net ultrasonic wave that travels along a preferred vector direction and is focused at a selected point along the beam. Conventional ultrasound imaging systems may also use other focusing strategies. For example, the ultrasound imaging system may control the transducer elements to emit a plane wave. Multiple firings may be used to acquire data representing the same anatomical information. The beamforming parameters of each of the firings may be varied to provide a change in maximum focus or otherwise change the content of the received data for each firing, e.g., by transmitting successive beams with the focal point of each beam being shifted relative to the focal point of the previous beam. By changing the time delay (or phase) of the applied pulses, the beam with its focal point can be moved to scan the object.

The same principles apply when the transducer array is employed to receive the reflected sound energy. The voltages produced at the receiving elements are summed so that the net signal is indicative of the ultrasound reflected from a single focal point in the object. As with the transmission mode, this focused reception of the ultrasonic energy is achieved by imparting a separate delay and gain to the signal from each receiving element. For receive beam-forming, this is done in a dynamic manner in order to focus appropriately for the depth range in question.

Many conventional ultrasound imaging systems that are capable of acquiring 4D ultrasound data have included a two-dimensional transducer array (hereinafter a 2D transducer array). For purposes of this disclosure, a 2D transducer array is defined to include a transducer array where the center points of the transducer elements form a two-dimensional pattern. The two-dimensional pattern may follow a curved surface according to some embodiments. The transducer elements may be dimensionally generally similar in both length and width in a 2D transducer array, or have other aspect ratios. Additionally, a 2D transducer array has electronic focusing and steering. The 2D transducer array typically comprises a number of transducer elements arranged in a grid; the grid may have a square, rectangular, hexagonal, or other basis. By controlling the timing and amplitude of the elements in the 2D transducer array, it is possible to steer the transmitted ultrasound beam simultaneously in both an azimuth direction and in an elevation direction. The beam control can of course be derived in any chosen coordinate system. The use of a 2D transducer array allows the ultrasound transducer or probe to have greater flexibility and it enables greater accuracy in the acquisition of volumetric data.

During acquisition of volumetric ultrasound data it is often a challenge to get both sufficient frame rate and lateral resolution for the desired volume of interest. A common way to improve frame rate and/or lateral resolution is to acquire the entire volume as a set of sub-volumes. The acquisition of the sub-volumes may be gated to a physiological signal, such as an ECG signal. Acquiring gated volumetric ultrasound data of a patient's heart has two key challenges. The first challenge is that since it may take multiple heart cycles to acquire a complete volume of data, the display may show inconsistent data when the operator moves the probe in search of the correct view and good access. As the operator moves the probe, the image shown on the display may be generated from sub-volumes that were acquired at a previous probe position. In other words, the image on the display may not accurately reflect the real-time position of the probe. This may make it difficult for the operator to know if the new probe position is an improvement over one or more older probe positions. The second challenge is that if the probe and/or the heart move with respect to each other over several cardiac cycles, the ultrasound data may become prone to artifacts.

For these and other reasons an improved system and method of volumetric ultrasound imaging is desired.

BRIEF DESCRIPTION OF THE INVENTION

The above-mentioned shortcomings, disadvantages and problems are addressed herein which will be understood by reading and understanding the following specification.

In an embodiment, a method of ultrasound imaging includes acquiring volumetric data of a volume of interest with an ultrasound imaging system. The method includes acquiring planar data with the ultrasound imaging system during the process of acquiring the volumetric data, the planar data including data of a plane through the volume of interest. The method includes displaying a reference image based on the planar data during the process of acquiring the volumetric data. The method also includes displaying an image based on the volumetric data.

In another embodiment, a method of ultrasound imaging includes acquiring a plurality of volumetric datasets of a volume of interest with an ultrasound imaging system. The method includes iteratively acquiring planar data with the ultrasound imaging system in between acquiring the plurality of volumetric datasets, the planar data comprising data of a plane through the volume of interest. The method includes displaying a reference image based on the planar data during the process of acquiring the plurality of volumetric datasets.

In another embodiment, an ultrasound imaging system includes a probe adapted to scan a volume of interest, a display and a processing unit in electronic communication with the probe and the display, wherein the processing unit is configured to control the probe to acquire volumetric data of a volume of interest. The processing unit is configured to control the probe to acquire planar data during the process of acquiring the volumetric data, the planar data including data of a plane through the volume. The processing unit is also configured to display a reference image on the display during the process of acquiring the volumetric data, the reference image being based on the planar data.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
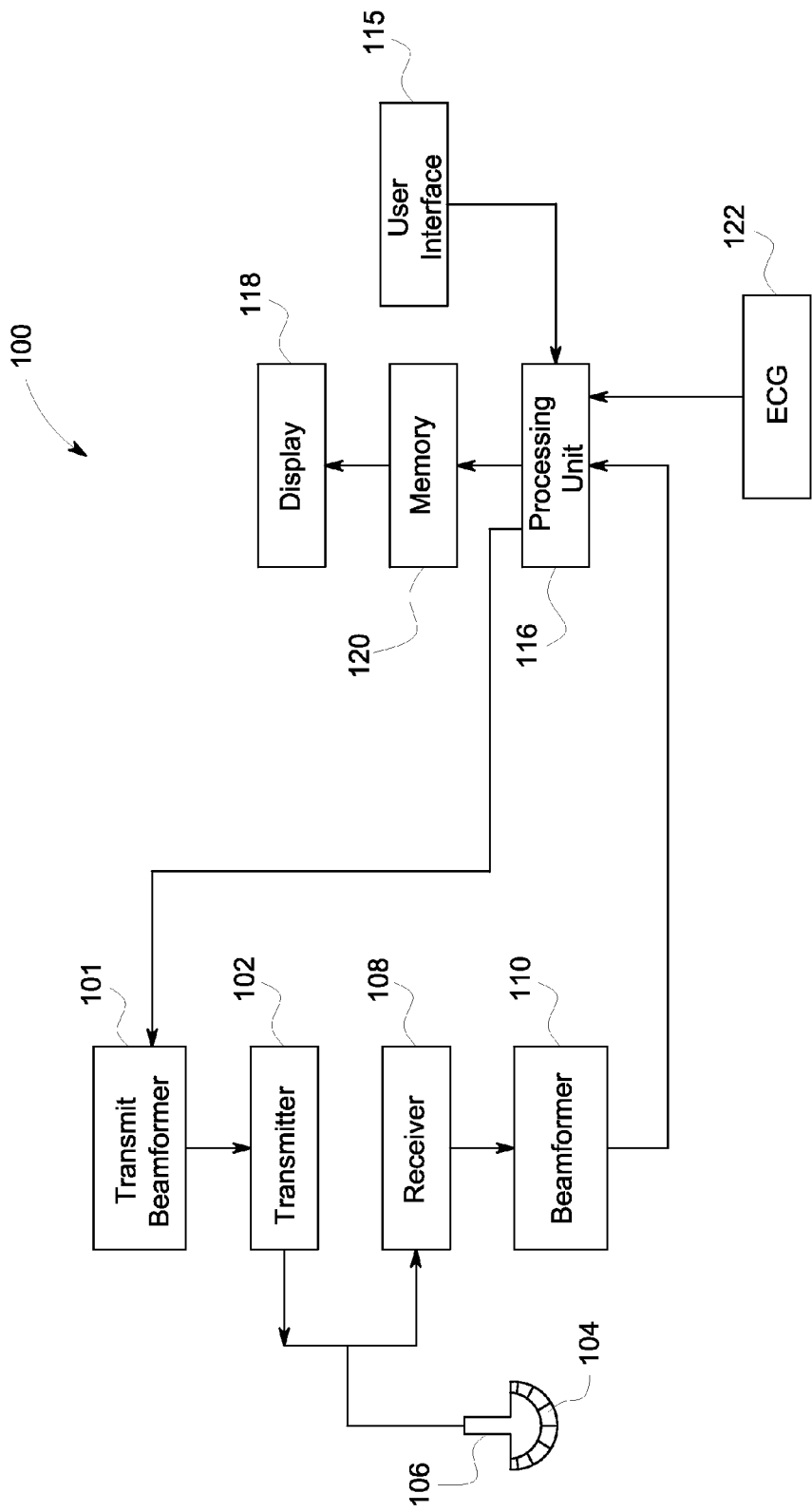
FIG. 1 is a schematic diagram of an ultrasound imaging system in accordance with an embodiment.

FIG. 1 is a schematic diagram of an ultrasound imaging system 100. The ultrasound imaging system 100 includes a transmit beamformer 101 and a transmitter 102 that drive transducer elements 104 within a probe 106 to emit pulsed ultrasonic signals into a body (not shown). A variety of geometries of probes and transducer elements may be used. The pulsed ultrasonic signals are back-scattered from structures in the body, like blood cells or muscular tissue, to produce echoes that return to the transducer elements 104. The echoes are converted into electrical signals, or ultrasound data, by the transducer elements 104 and the electrical signals are received by a receiver 108. According to some embodiments, the probe 106 may contain electronic circuitry to do all or part of the transmit and/or the receive beam forming. For example, all or part of the transmit beamformer 101, the transmitter 102, the receiver 108 and the beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. The electrical signals representing the received echoes are passed through a beam-former 110 that outputs ultrasound data. A user interface 115 may be used to control operation of the ultrasound imaging system 100, including, to control the input of patient data, to change a scanning or display parameter, and the like.

The ultrasound imaging system 100 also includes a processing unit 116 to control the transmit beamformer 101, the transmitter 102, the receiver 108 and the beamformer 110. The processing unit 116 is in electronic communication with the probe. The processing unit 116 controls which of the transducer elements are active and the shape of a beam emitted from the probe 106. The processing unit is also in electronic communication with a display 118, and the processing unit 116 may process the data into images for display on the display 118. The processing unit 116 may comprise a central processing unit (CPU) according to an embodiment. According to other embodiments, the processing unit 116 may comprise other electronic components capable of carrying out processing functions, such as a digital signal processor, a field-programmable gate array (FPGA) or a graphic board. According to other embodiments, the processing unit 116 may comprise multiple electronic components capable of carrying out processing functions. For example, the processing unit 116 may comprise two or more electronic components selected from a list of electronic components including: a central processing unit, a digital signal processor, a field-programmable gate array, and a graphic board. According to another embodiment, the processing unit 116 may also include a complex demodulator (not shown) that demodulates the RF data and generates raw data. In another embodiment the demodulation can be carried out earlier in the processing chain. The processing unit 116 is adapted to perform one or more processing operations according to a plurality of selectable ultrasound modalities on the data. The ultrasound data may be processed in real-time during a scanning session as the echo signals are received. For the purposes of this disclosure, the term "real-time" is defined to include a procedure that is performed without any intentional delay. For example, an embodiment may acquire and display images with a real-time frame-rate of 7-20 frames/sec. However, it should be understood that the real-time frame rate may be dependent on the length of time that it takes to acquire each frame of ultrasound data for display. Accordingly, when acquiring a relatively large volume of data, the real-time frame rate may be slower. Thus, some embodiments may have real-time frame-rates that are considerably faster than 20 frames/sec while other embodiments may have real-time frame-rates slower than 7 frames/sec. The ultrasound information may be stored temporarily in a buffer (not shown) during a scanning session and processed in less than real-time in a live or off-line operation. Some embodiments of the invention may include multiple processing units (not shown) to handle the processing tasks. For example, a first processing unit may be utilized to demodulate and decimate the RF signal while a second processing unit may be used to further process the data prior to displaying an image. It should be appreciated that other embodiments may use a different arrangement of processing units.

The ultrasound imaging system 100 may continuously acquire data at a frame-rate of, for example, 10 Hz to 30 Hz. Images generated from the data may be refreshed at a similar frame rate. Other embodiments may acquire and display data at different rates. For example, some embodiments may acquire data at a frame rate of less than 10 Hz or greater than 30 Hz depending on the size of the volume and the intended application. A memory 120 is included for storing processed frames of acquired data. In an exemplary embodiment, the memory 120 is of sufficient capacity to store at least several seconds worth of frames of ultrasound data. The frames of data are stored in a mariner to facilitate retrieval thereof according to its order or time of acquisition. The memory 120 may comprise any known data storage medium. There is an ECG 122 attached to the processing unit 116 of the ultrasound imaging system 100 shown in FIG. 1. The ECG may be connected to the patient and provides cardiac data from the patient to the processing unit 116 for use during the acquisition of gated data.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processing unit 116 (e.g., B-mode, Color Doppler, M-mode, Color M-mode, spectral Doppler, TVI, strain, strain rate, and the like) to form 2D or 3D data. For example, one or more modules may generate B-mode, color Doppler, M-mode, color M-mode, spectral Doppler, TVI, strain, strain rate and combinations thereof, and the like. The image beams and/or frames are stored and timing information indicating a time at which the data was acquired in memory may be recorded. The modules may include, for example, a scan conversion module to perform scan conversion operations to convert the image frames from coordinates beam space to display space coordinates. A video processor module may be provided that reads the image frames from a memory and displays the image frames in real time while a procedure is being carried out on a patient. A video processor module may store the image frames in an image memory, from which the images are read and displayed.

Figure 2:
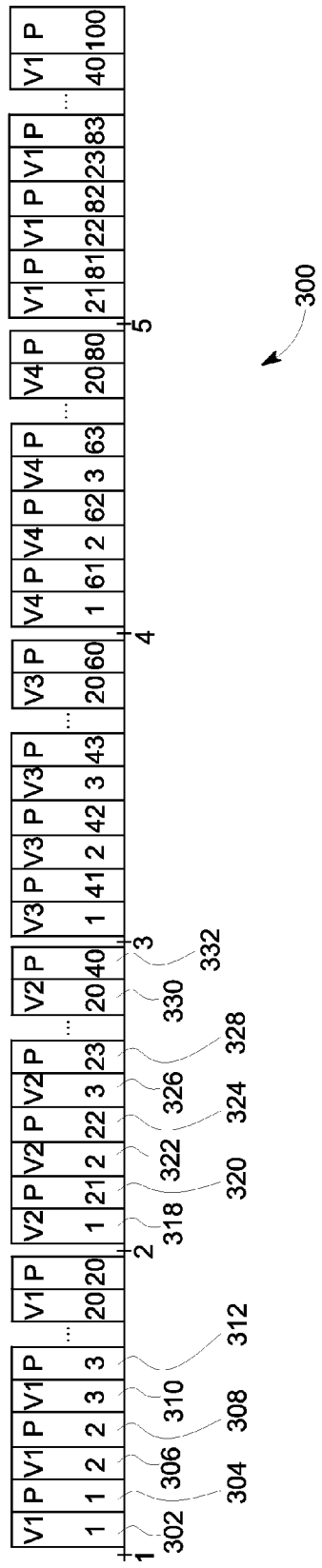
FIG. 2 is a schematic representation of a timeline for the acquisition of both volumetric data and planar data in accordance with an embodiment.

FIG. 2 is schematic representation of a timeline for the acquisition of both volumetric data and planar in accordance with an embodiment. The method represented by the timeline in FIG. 3 may be performed with an ultrasound imaging system such as the ultrasound imaging system 100 shown in FIG. 1. The planar data may comprise either two-dimensional data or a slab of data of a plane in a volume of interest. The planar data contains information about a plane either in or extending through the volume of interest. For example, according to an embodiment, the planar data may contain information about the region beyond the volume of interest. In other words, an image of a plane may be generated from the planar data that shows both a cross-section through the volume of interest as well as structure in a region extending outside the boundaries of the volume of interest. The technical effect of the method illustrated in the timeline of FIG. 2 is the display of a reference image during the process of acquiring volumetric data.

Referring to FIG. 2, the timeline 300 shows the order of acquisition of volumetric data and planar data according to an exemplary embodiment. According to an embodiment, the volumetric data may include a plurality of volumetric datasets and the planar data may include a plurality of planar datasets. Also, according to the exemplary embodiment, the volumetric data for the volume of interest may be acquired as four separate sub-volumes. This may be particularly useful when imaging a large volume, as the volumetric data corresponding to each of the sub-volumes can be acquired in much less time than it would take to acquire volumetric data of the whole volume. Each of the rectangles labeled with a "V" represents a volumetric dataset and each of the rectangles labeled with a "P" represents a planar dataset. In the timeline 300, the volumetric datasets are further labeled with the number "1", "2", "3", or "4" after the "V". The number "1", "2", "3", or "4" indicates the specific sub-volume from which the volumetric dataset was acquired. For example, volumetric datasets labeled with a "1" correspond to a first sub-volume; volumetric datasets labeled with a "2" correspond to a second sub-volume; volumetric datasets labeled with a "3" correspond to a third sub-volume; and, volumetric datasets labeled with a "4" correspond to the fourth sub-volume. All of the datasets are also labeled with a number underneath the "P" or "V". The number underneath the "P" or "V" indicates the iteration of the acquisition. For example, volumetric dataset 302 is labeled V1; 1. The "V" indicates that the dataset is a volumetric dataset. The "1" after the V indicates that the dataset contains information about the first sub-volume. The "1" beneath the "V1" indicates that the volumetric dataset 202 is the first iteration of the acquisition of a volumetric dataset of the first sub-volume. Additional description about the events in the timeline 300 will be provided hereinafter.

The volumetric dataset 302 of the first sub-volume is acquired during a first portion of a patient's first cardiac cycle. A planar dataset 304 is acquired after the acquisition of the volumetric dataset 302. Volumetric dataset 306 of the first sub-volume is acquired after planar dataset 304. Planar dataset 308 is acquired next, followed by the acquisition of volumetric dataset 310 of the first sub-volume and planar dataset 312. According to an embodiment, the processing unit 116 (shown in FIG. 1) controls the probe to alternate between acquiring a volumetric dataset and a planar dataset throughout the whole first cardiac cycle. According to the embodiment shown in FIG. 2, the processing unit 116 controls the probe 106 (shown in FIG. 1) to acquire 20 volumetric datasets covering the first sub-volume and 20 planar datasets during the first cardiac cycle. During the first cardiac cycle, volumetric datasets are acquired for the first sub-volume at 20 different times during the cardiac cycle. Additionally, an updated planar dataset is acquired after each of the volumetric datasets in accordance with an embodiment.

Still referring to FIG. 2, during the second cardiac cycle, 20 additional volumetric datasets are acquired of the second sub-volume. An updated planar dataset is also acquired after each of the 20 volumetric datasets. According to an embodiment, the planar datasets acquired during the second cardiac cycle may include data of the same plane as the planar datasets acquired during the first cardiac cycle. The processing unit 116 (shown in FIG. 1) controls the probe to alternate between acquiring a volumetric dataset of the second sub-volume and acquiring a planar dataset during the second cardiac cycle. For example, volumetric dataset 318 of the second sub-volume is acquired, followed by planar dataset 320. Next, volumetric dataset 322 of the second sub-volume is acquired, followed by planar dataset 324. Then, volumetric dataset 326 of the second sub-volume is acquired, followed by planar dataset 328. This pattern of alternating between the acquisition of a volumetric dataset of the second sub-volume and the acquisition of a planar dataset continues until the acquisition of volumetric dataset 330 and planar dataset 332 have been acquired during the second cardiac cycle.

During the third cardiac cycle, 20 volumetric datasets for the third sub-volume and 20 planar datasets are alternately acquired in a similar manner to that which was previously described for the first and second cardiac cycles. That is, the processing unit 116 (shown in FIG. 1) controls the probe 106 to alternate between acquiring a volumetric dataset of the third sub-volume and acquiring a planar dataset during the third cardiac cycle. According to the embodiment shown in FIG. 2, all of the volumetric datasets shown in the third cardiac cycle contain volumetric ultrasound data of the third sub-volume. Likewise, during the fourth cardiac cycle, 20 volumetric datasets of the fourth sub-volume and 20 planar datasets are alternately acquired in a similar pattern to that described hereinabove for the first three cardiac cycles.

According to an exemplary embodiment, after 4 cardiac cycles, volumetric ultrasound data has been collected at 20 different phases of the cardiac cycle for all four sub-volumes. According to an embodiment, a cardiac monitoring device, such as an ECG, may be attached to the patient during the acquisition of the datasets. The processing unit 116 (shown in FIG. 1) may use signals from the ECG to gate the acquisition of the each of the volumetric datasets. By using a cardiac monitoring device, the processing unit 116 can ensure that the volumetric datasets are acquired at generally consistent phases during multiple cardiac cycles. It should be appreciated by those skilled in the art that other embodiments may require a different number of sub-volumes in order to completely cover a volume of interest, such as the heart. Those skilled in the art will appreciate that after four cardiac cycles, it is possible to generate and display an image of the heart including all four sub-volumes according to the embodiment shown in FIG. 2. Additionally, since volumetric data were acquired at 20 different phases for each of the sub-volumes, by stitching together the volumetric data based on cardiac phase, it is possible to generate a "live" or dynamic image of the whole heart. The dynamic image may include a loop showing the heart at multiple phases during a whole cardiac cycle.

According to the embodiment shown in FIG. 2, the processing unit 116 may control the acquisition of volumetric datasets so that the pattern of the first four cardiac cycles is repeated throughout the acquisition. For example, the timeline 300 shows that during the fifth cardiac cycle, the processing unit 116 controls the acquisition so that volumetric datasets of the first sub-volume (shown in FIG. 2) are acquired. According to an embodiment, the acquisition of data during the fifth cardiac cycle is exactly the same as it was in the first cardiac cycle. As described previously, after the first four cardiac cycles, there is enough data to show a dynamic image of the whole heart over a complete cardiac cycle. During the fifth cardiac cycle, additional volumetric datasets are acquired of the first sub-volume. While the volumetric datasets acquired during the fifth cardiac cycle all represent the same sub-volume, namely the first sub-volume, that was acquired during the first cardiac cycle, they are at a later point in time. Therefore, according to an embodiment, a dynamic image of the heart may continuously be updated as additional volumetric datasets are acquired. For example, the volumetric datasets acquired during the fifth cardiac cycle may replace the volumetric datasets acquired during the first cardiac cycle. In this way, the dynamic image of the heart may be continuously be updated as long as additional volumetric ultrasound data is being acquired. Those skilled in the art should appreciate that if it is desired to update the dynamic image in a continuous fashion, the updated data will only affect one sub-volume at a time according to the embodiment shown in FIG. 2. While only the first five cardiac cycles are shown in FIG. 2, it should be appreciated that the pattern of acquiring volumetric data and planar data may be continued for many additional cardiac cycles according to an embodiment.

According to the embodiment shown in FIG. 2, a planar dataset is acquired after each of the volumetric datasets. A planar dataset may take significantly less time to acquire than a volumetric dataset since the planar dataset comprises either a two-dimensional dataset or else a slab of data while the volumetric dataset typically contains three-dimensional data for a volume of interest. Both two-dimensional data and slab data typically take much less time to acquire than a volumetric dataset for a volume or sub-volume of a diagnostically useful size. For these reasons, the method illustrated by the timeline 300 may spend a majority of the time acquiring volumetric ultrasound data even though planar datasets are regularly acquired in between the acquisitions of volumetric ultrasound data. According to other embodiments, it may be desirable to acquire multiple volumetric datasets in between each acquisition of a planar dataset.

The embodiment shown in FIG. 2 includes iteratively acquiring planar data. As discussed hereinabove, the ultrasound data for the plane may be acquired for the same plane throughout an acquisition. For purposes of this disclosure, the plane is defined with respect to the transducer elements of the probe used to acquire the ultrasound data, such as the transducer elements 104 shown in FIG. 1. That is, the plane is spatially defined with respect to the total volume of interest that is being acquired by the probe at a given time. In other words, if the probe moves with respect to the patient or if the internal organs of the patient are displaced, the plane will include different anatomical regions at different points in time.

Since the planar data used to generate the reference image may be reacquired after acquiring each volumetric dataset, the processing unit 116 (shown in FIG. 1) is able to generate a reference image of the plane with a fast refresh rate—i.e. the reference image may be a dynamic image. For purposes of this disclosure, the term "dynamic image" is defined to include an image comprised of many individual images or frames that are displayed in sequence. The dynamic image may be refreshed or updated at different rates in accordance with different embodiments. Each image or frame of the dynamic image may be refreshed as new frames are generated based on updated data. According to an exemplary embodiment, a new frame may be generated based on each of the ultrasound datasets of the plane. As such, the dynamic image may be useful for showing any motion that occurs over a period of time. The example represented in FIG. 2 could result in a reference image of the plane with a refresh rate of up to 20 times per cardiac cycle. Using a reference image of the plane that is updated this quickly allows the user to gain real-time feedback about the position of the probe 106 (shown in FIG. 1) while acquiring the complete volume of interest over several cardiac cycles. In another embodiment the reference plane might be acquired between each second sub-volume to spend less time to acquire the reference planes. By reacquiring the plane at regular intervals during the more time-consuming acquisition of volumetric ultrasound data, it is possible to generate and display a reference image of the plane that is updated in real-time. Sonographers and other users of the system may use the dynamic reference image of the plane to validate a probe position and confirm whether or not the desired volumetric datasets are being acquired while in the process of acquiring the volumetric ultrasound data.

According to other embodiments, reference images for more than one plane may be acquired and displayed. For example, instead of acquiring planar data for just one plane during each cardiac cycle as shown in FIG. 2, planar data corresponding to multiple planes may be acquired during the process of acquiring volumetric data. For example, an embodiment may acquire first planar data of a first plane and second planar data of a second plane. This would allow the user to view a first reference image of the first plane and a second reference image of the second plane in order to gain additional information during the acquisition of volumetric ultrasound data. One embodiment may show a first dynamic image of a first plane and a second dynamic image of a second plane as part of a bi-plane view. The first plane and the second plane may be disposed at an angle to each other. Or, according to a specific embodiment, the first plane and the second plane may be generally perpendicular to each other. However, the processing unit 116 (shown in FIG. 1) may control the probe to alternate between acquiring planar data of a first plane in one cardiac cycle and acquiring planar data of a second plane during another cardiac cycle.

Additionally, the methods of other embodiments may acquire planar data for three or more planes that are displayed as three or more reference images. It should be appreciated by those skilled in the art that additional ways of interleaving the acquisition of volumetric data and the acquisition of planar data may be envisioned by those skilled in the art. For example, ultrasound imaging systems may acquire planar data at a faster rate for some planes than for other planes. Also, while the exemplary embodiments have described the acquisition of data with respect to a patient's cardiac cycle, it should be appreciated that the acquisition of volumetric data and planar data may be gated to other physiological cycles according to other embodiments.

The embodiment shown in FIG. 2 shows a method of an ECG gated acquisition of volumetric data that results in the display of an image of the heart. By acquiring a planar dataset in between acquiring each of the volumetric datasets, it is possible to show a reference image of the plane that updates more quickly than the total volume of interest. As described hereinabove, the plane may be defined with respect to the ultrasound probe according to an embodiment. Therefore, any relative movement between the probe and the desired volume of interest will be readily apparent to the user during the acquisition. The reference image of the plane may be used to accurately position the probe during the acquisition of volumetric data. Each frame of the reference image corresponds to a specific cross-section through the volume of interest with respect to the probe. The user may position the plane so that it passes through the sub-volume being acquired in order to check for movement or artifacts. Since the reference image of the plane is updated multiple times during the acquisition of a volume of interest, the reference image of the plane provides useful real-time feedback to an operator of the ultrasound imaging system. The operator may use the reference image of the plane to validate probe position of the probe 106 (shown in FIG. 1) during the acquisition of the volumetric data. The operator may also use the reference image to check the quality of the volumetric data during the acquisition of the volumetric data. For example, if the reference image were to show some type of obstruction or an incorrect view of the anatomical structure, the operator would know that the volumetric data currently being acquired is no longer likely to be valid. In another embodiment, the processing unit 116 may check the quality of the volumetric data by comparing an image generated from the volumetric data to the reference image. For example, the operator may compare a reference image of a plane to an image of the same plane generated from volumetric data. Any significant differences between the two images may indicate a potential problem with the volumetric data. Also, since the reference image provides the operator with this feedback much more quickly than waiting for the entire volume to acquired and then displayed, the operator can make the appropriate corrections in much less overall time. An advantage of this technique may therefore include a reduction in the time needed for an operator to successfully complete an exam, which, in turn, may result in an increase in patient comfort.

Figure 3:
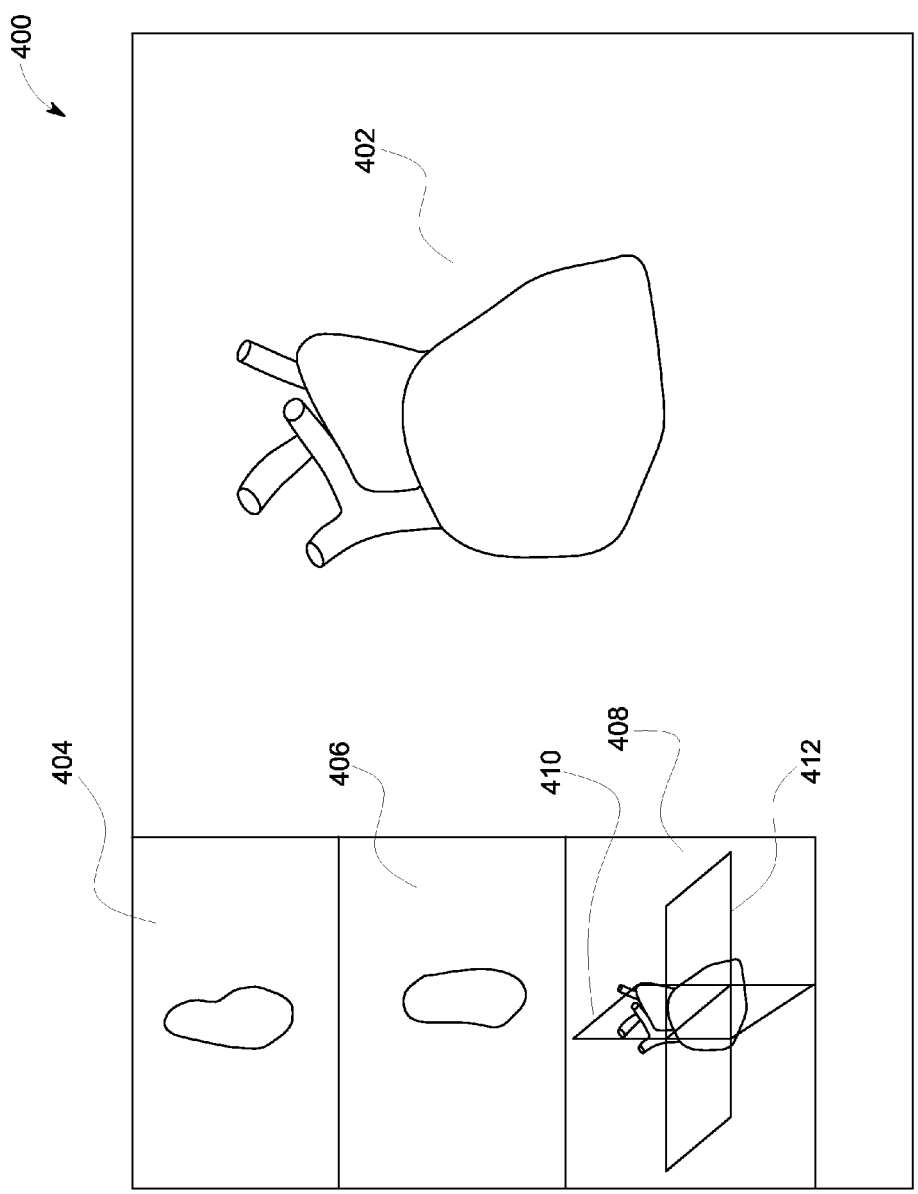
FIG. 3 is a schematic representation of a screenshot of a display in accordance with an embodiment.

FIG. 3 is a schematic representation of a screenshot 400 of a display in accordance with an embodiment. The display may be part of an ultrasound imaging system such as the ultrasound imaging system 100 shown in FIG. 1. The screenshot 400 includes an image 402. The image 402 is generated from volumetric ultrasound data. According to an embodiment, the image 402 may comprise a dynamic image. When used while scanning, the area occupied by the image 402 may show a dynamic image that changes as additional volumetric datasets are acquired. Or, according to other embodiments, the image 402 may show a static loop of frames that were previously acquired and saved in a memory. The screenshot 400 also includes a first reference image 404 and a second reference image 406. According to an embodiment, the first reference image 404 may comprise a first dynamic image of a first plane within a volume of interest. The second reference image 406 may comprise a second dynamic image of a second plane within the volume of interest. The first reference image 404 and the second reference image 406 may both refresh as additional datasets of the first plane and the second plane are acquired. According to the embodiment shown in FIG. 3, the first reference image 404 may show a first plane 410 that is generally perpendicular to a second plane 412. A reference icon 408 may show the relative positioning of the first plane 410 and the second plane 412 with respect to a volume. In other embodiments an image and one or more reference images may be arranged differently on the display. Also, the display may only show a reference image during the period of time before enough volumetric data has been acquired to show an image generated from the volumetric data.

Figure 4:
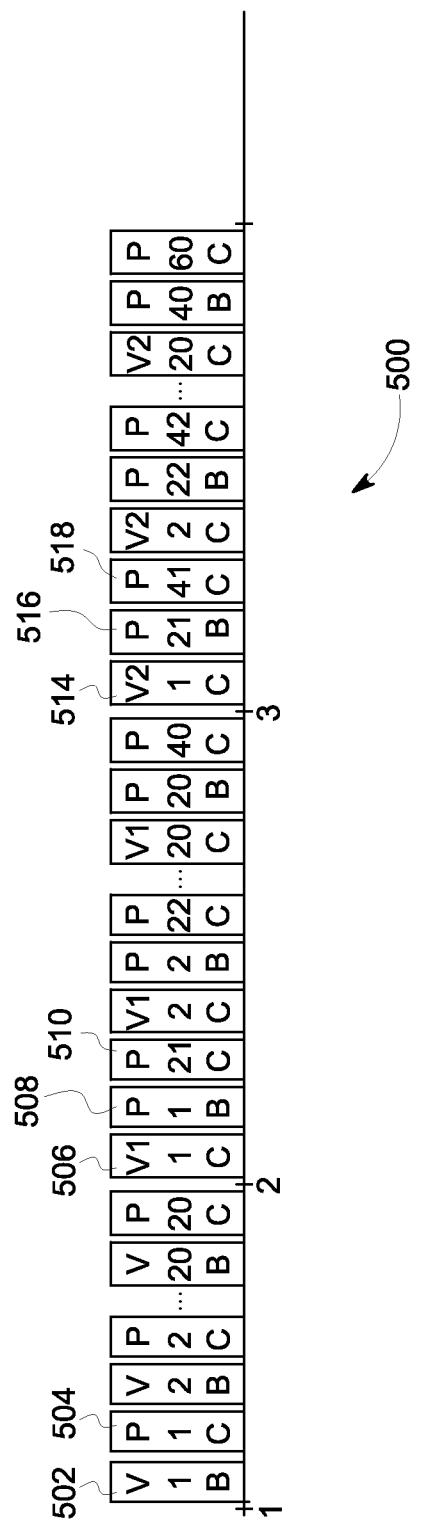
FIG. 4 is a schematic representation of a timeline for the acquisition of both volumetric data and planar data in accordance with an embodiment.

FIG. 4 is a schematic representation of a timeline of the acquisition of both volumetric data and planar data in accordance with an embodiment. An ultrasound imaging system, such as the ultrasound imaging system 100 may be used to (shown in FIG. 1) acquire data according to the method depicted in the timeline 500. The technical effect of the method shown in the timeline 500 is the acquisition of planar data while in the process of acquiring volumetric data.

Referring to FIG. 4, the rectangles in the timeline 500 are coded in the same way as the rectangles in the timeline 300 from FIG. 2. However, in addition to the symbols used in FIG. 2, the rectangles in FIG. 4 also have a "B" or a "C" in the bottom of each rectangle. The "B" stands for a b-mode dataset while the "C" stands for a colorflow dataset. Both b-mode and colorflow mode are examples of ultrasound imaging modes. Hereinafter, the terms "colorflow" and "b-mode" may be used to help clarify the types of datasets shown in the timeline 300. However, it should be appreciated that other embodiments may acquire data with additional ultrasound imaging modes.

In accordance with an embodiment, volumetric dataset 502 is acquired first. The volumetric dataset 502 comprises b-mode data of a volume including the whole heart. After the acquisition of the volumetric dataset 502, planar dataset 504 is acquired. The planar dataset 504 comprises colorflow data of a plane. During the first cardiac cycle, b-mode volumetric datasets, such as the volumetric dataset 502, and colorflow planar datasets, such as the planar dataset 504, are alternately acquired. According to the embodiment shown in timeline 500, 20 b-mode volumetric datasets and 20 colorflow planar dataset are acquired during the first cardiac cycle. Therefore, at the end of the first cardiac cycle, b-mode data has been acquired for the heart at 20 different cardiac phases. Likewise, colorflow planar data has been acquired at 20 different cardiac phases. While the embodiment in FIG. 4 shows the acquisition of 20 volumetric datasets and 20 planar datasets, it should be appreciated that other embodiments may acquire a different number of datasets during a cardiac cycle. The time required to acquire each of the colorflow volumetric datasets may also affect the total number of datasets that are acquired during a single cardiac cycle. For example, if the acquisition volume is larger in size, each volumetric dataset may take longer to acquire. Therefore, it may only be possible to acquire fewer volumetric datasets during the first cardiac cycle. Conversely, if the acquisition volume is smaller in size, it may be possible to acquire substantially more than 20 volumetric datasets during the first cardiac cycle.

During the second cardiac cycle, volumetric dataset 506 is acquired. The volumetric dataset 506 comprises colorflow data of a first sub-volume of a volume of interest. After the acquisition of the volumetric dataset 506, planar dataset 508 is acquired. Planar dataset 508 comprises b-mode data about the same plane included in the planar dataset 504. Next, planar dataset 510 may be acquired. Planar dataset 510 comprises colorflow data about the same plane that was included in the planar datasets 504 and 508. According to the embodiment shown in FIG. 4, additional datasets are acquired according to the same pattern during the rest of the second cardiac cycle. That is, the data is acquired in the pattern of a colorflow volumetric dataset of the first sub-volume, such as volumetric dataset 506, followed by a b-mode planar dataset, such as planar dataset 508, followed by a colorflow planar dataset, such as planar dataset 510. According to the embodiment depicted in the timeline 500, this pattern is repeated 20 times during the second cardiac cycle. At the end of the second cardiac cycle, 20 colorflow volumetric datasets of the first sub-volume, such as volumetric dataset 506, have been acquired of the first sub-volume. Additionally, 20 b-mode planar datasets, such as planar dataset 508, and 20 additional colorflow planar datasets, such as planar dataset 510, have been acquired. During the second cardiac cycle, both b-mode and colorflow planar data are acquired during the process of acquiring volumetric data. It should be noted that FIG. 4 shows just one way of interleaving the acquisition of first planar data and second planar data with the acquisition of volumetric data.

During the third cardiac cycle, a volumetric dataset 514 is acquired. The volumetric dataset 514 comprises colorflow data of a second sub-volume of the volume of interest. According to an embodiment, the second sub-volume may comprise approximately one half of the patient's heart, and the combination of the first sub-volume and the second sub-volume may cover all of the patient's heart. After the acquisition of the first volumetric dataset 514, planar dataset 516 is acquired. The planar dataset 516 may be of the same plane as that included in the planar datasets acquiring during the second cardiac cycle. Next, planar dataset 518 is acquired. The planar dataset 518 comprises a colorflow dataset of the plane. According to the embodiment shown in FIG. 4, additional datasets are acquired according to the same pattern during the rest of the third cardiac cycle. That is, the data is acquired in the pattern of a colorflow volumetric dataset of the second sub-volume, such as volumetric dataset 514, followed by a b-mode planar dataset, such as planar dataset 516 followed by a colorflow planar dataset 518. According to the embodiment depicted in the timeline 500, this pattern is repeated 20 times during the third cardiac cycle. Therefore, during the third cardiac cycle, 20 colorflow volumetric datasets are acquired of the first sub-volume, 20 b-mode ultrasound datasets of the plane, and 20 colorflow ultrasound datasets of the plane are acquired.

According to an embodiment, the method shown in the timeline 500 may repeat the pattern of acquisition shown in the second and third cardiac cycles multiple times after the third cardiac cycle. For instance, during the fourth cardiac cycle, data may be acquired in the same pattern as in the second cardiac cycle. Then, during the fifth cardiac cycle, data may be acquired in the same pattern as in the third cardiac cycle. Therefore, after a number of cardiac cycles, the method will have acquired multiple colorflow volumetric datasets for both the first sub-volume and the second sub-volume during a plurality of different cardiac cycles. Additionally, the acquisition of colorflow planar data and b-mode colorflow data will be interleaved with the acquisition of the colorflow volumetric data.

Still referring to FIG. 4, the processing unit 116 (shown in FIG. 1) may display a reference image based on the planar data acquired during the first cardiac cycle. The reference image may be a dynamic image of a plane showing colorflow data. The reference image may update in real-time as additional planar datasets are acquired during the first cardiac cycle while the volumetric datasets are acquired. During the first cardiac cycle, b-mode volumetric data is acquired for the entire volume. A dynamic b-mode image based on the volumetric data may be displayed during the first cardiac cycle. Those skilled in the art should appreciate that both the reference image and the image based on the volumetric data may be updated in real-time as additional planar datasets and volumetric datasets are acquired. A user may use images generated from the volumetric data in the first cardiac cycle and the reference image generated from the planar data in order to ensure that the probe is placed appropriately in order to capture the desired colorflow data during subsequent cardiac cycles. As described above, the planar data comprises colorflow data, so the user is able to use the reference image showing the colorflow data of the plane as a further check regarding the location of the probe and the volume of interest.

The volumetric data acquired during the second cardiac cycle is colorflow data of the first sub-volume. According to the embodiment described with respect to FIG. 4, the volumetric data for the second sub-volume isn't acquired until the third cardiac cycle. It will therefore take at least two cardiac cycles to acquire colorflow volumetric data for the entire heart at all twenty phases. To improve flow framerate (volumerate) or flow quality it may be desirable to acquire from 2 to 7 colorflow volumetric datasets at each phase before displaying a colorflow image. However, since the method acquires colorflow planar data and b-mode planar data during the process of acquiring the volumetric data, a b-mode reference image and a colorflow reference image may be displayed. Both the b-mode reference image and the colorflow reference image may be dynamic images that update in real-time. An operator may use the reference images to validate a probe position during the acquisition of the volumetric data, which as mentioned previously, may take several cardiac cycles. The operator would gain real-time feedback if the probe was no longer correctly positioned by checking the reference images rather than waiting several cardiac cycles only to find out that the acquired volumetric data was not of the intended imaging target. Additionally, the operator may have the advantage of viewing a reference image showing a b-mode image of a plane and a second reference image showing a colorflow image of the plane at generally the same time. The b-mode reference image may show anatomical structure more clearly while the colorflow image may be used to ensure that the colorflow volumetric data is capturing the intended fluid movement.

According another embodiment, planar data for two or more different planes through the volume of interest may be acquired. For example, first planar data may be acquired of a first plane and second planar data may be acquired of a second plane during the process of acquiring volumetric data. A first reference image based on the first planar data and a second reference image based on the second planar data may be used by the operator in order to gain an additional perspective on the current position of the probe. According to an embodiment, the first plane may be disposed at a generally perpendicular angle with respect to the second plane. Additionally, the first reference image and the second reference image may be displayed in a bi-plane view, similar to that used during a conventional bi-plane mode.

The method described with respect to FIG. 4 includes b-mode and colorflow as the first ultrasound imaging mode and the second ultrasound imaging mode respectively. Both the volumetric datasets and the planar datasets include a first ultrasound imaging mode, that is b-mode, and a second ultrasound imaging mode, that is colorflow. Other embodiments may include ultrasound imaging modes other than b-mode and colorflow.

It should be appreciated that other embodiments may use a different pattern of acquiring ultrasound datasets than the one illustrated in FIG. 4. For example, the planar datasets may be acquired either a slower or a faster rate. As long as the reference image refreshes at a faster rate than an image generated from the volumetric data, the reference image may be useful for validating a probe position for the acquisition of volumetric ultrasound data. Additionally, other embodiments may interleave the acquisition of volumetric datasets and planar datasets in a different manner.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method of ultrasound imaging comprising:
acquiring first volumetric data of a volume of interest with a probe that is a component of an ultrasound imaging system during a first cardiac cycle while the ultrasound imaging system is in a first imaging mode;
displaying a first image based on all of the first volumetric data;
positioning the probe using the first image;
acquiring second volumetric data with the probe after said positioning the probe, where the second volumetric data is acquired for multiple cardiac cycles after the first cardiac cycle while the ultrasound imaging system is a second imaging mode that is different from the first imaging mode;
acquiring second planar data of a plane through the volume of interest with the probe during the process of acquiring the second volumetric data, where the ultrasound imaging system is in the first imaging mode while acquiring the second planar data;
displaying a second reference image generated from the second planar data during the process of acquiring the second volumetric data; and
displaying a second image based on all of the second volumetric data.

2. The method of claim 1, wherein the first imaging mode is one of colorflow and B-mode, and the second imaging mode is the other of colorflow and B-mode.

3. The method of claim 1, wherein acquiring the second planar data comprises interleaving the acquisition of the second planar data with the acquisition of the second volumetric data.

4. The method of claim 1, further comprising acquiring first planar data of the plane through the volume of interest during the process of acquiring the first volumetric data, where the first planar data is acquired with the ultrasound imaging system in the second imaging mode.

5. An ultrasound imaging system comprising:
a probe adapted to scan a volume of interest;
a display; and
a processing unit in electronic communication with the probe and the display, wherein the processing unit is configured to:
control the probe to acquire first volumetric data of a volume of interest during a first cardiac cycle while the ultrasound imaging system is in a first imaging mode;
control the probe to acquire first planar data through the volume of interest during the process of acquiring the first volumetric data, where the ultrasound imaging system is in a second imaging mode that is different from the first imaging mode while acquiring the first planar data;
displaying a first reference image based on the first planar data on the display during the process of acquiring the first volumetric data;
displaying a first image based on the first volumetric data on the display;
control the probe to acquire second volumetric data after displaying the first reference image and the first image, wherein the second volumetric data is acquired for multiple cardiac cycles after the first cardiac cycle, and where the ultrasound imaging system is in the second imaging mode while the second volumetric data is acquired;
control the probe to acquire second planar data of a plane through the volume of interest during the process of acquiring the second volumetric data, where the ultrasound imaging system is in the first imaging mode while acquiring the second planar data;
display a second reference image generated from the second planar data on the display during the process of acquiring the second volumetric data; and
display a second image based on the second volumetric data on the display.

6. An ultrasound imaging system comprising:
a probe adapted to scan a volume of interest;
a display; and
a processing unit in electronic communication with the probe and the display, wherein the processing unit is configured to:
control the probe to acquire first volumetric data of a volume of interest during a first cardiac cycle while the ultrasound imaging system is in a first imaging mode;
control the probe to acquire first planar data through the volume of interest during the process of acquiring the first volumetric data, where the ultrasound imaging system is in a second imaging mode that is different from the first imaging mode while acquiring the first planar data;
display a first reference image based on the first planar data on the display during the process of acquiring the first volumetric data;
display a first image based on the first volumetric data on the display at the same time as the first reference image;
control the probe to acquire second volumetric data after displaying the first reference image and the first image, wherein the second volumetric data is acquired for multiple cardiac cycles after the first cardiac cycle, and where the ultrasound imaging system is in the second imaging mode while the second volumetric data is acquired;
control the probe to acquire second planar data of a plane through the volume of interest during the process of acquiring the second volumetric data, where the ultrasound imaging system is in the first imaging mode while acquiring the second planar data;

display a second reference image generated from the second planar data on the display during the process of acquiring the second volumetric data; and
display a second image based on the second volumetric data on the display.

7. An ultrasound imaging system comprising:
a probe adapted to scan a volume of interest;
a display; and
a processing unit in electronic communication with the probe and the display, wherein the processing unit is configured to:
control the probe to acquire first volumetric data of a volume of interest during a first cardiac cycle while the ultrasound imaging system is in a first imaging mode;
control the probe to acquire first planar data through the volume of interest during the process of acquiring the first volumetric data, where the ultrasound imaging system is in a second imaging mode that is different from the first imaging mode while acquiring the first planar data wherein the first imaging mode comprises one of B-mode and colorflow, and wherein the second imaging mode comprises the other of B-mode and colorflow;
display a first reference image based on the first planar data on the display during the process of acquiring the first volumetric data;
display a first image based on the first volumetric data on the display;
control the probe to acquire second volumetric data after displaying the first reference image and the first image, wherein the second volumetric data is acquired for multiple cardiac cycles after the first cardiac cycle, and where the ultrasound imaging system is in the second imaging mode while the second volumetric data is acquired;
control the probe to acquire second planar data of a plane through the volume of interest during the process of acquiring the second volumetric data, where the ultrasound imaging system is in the first imaging mode while acquiring the second planar data;
display a second reference image generated from the second planar data on the display during the process of acquiring the second volumetric data; and
display a second image based on the second volumetric data on the display.

8. A method of ultrasound imaging comprising:
acquiring first volumetric data of a volume of interest with a probe that is a component of an ultrasound imaging system by acquiring a first plurality of sub-volumes with an ultrasound imaging system during a first cardiac cycle, each of the first plurality of sub-volumes representing a different portion of the volume of interest, where the first volumetric data is acquired with the ultrasound imaging system in an imaging mode selected from group consisting of B-mode, color Doppler, color M-mode, TVI, strain, and strain rate;
iteratively acquiring first planar data of a plane through the volume-of interest with the ultrasound imaging system in between acquiring each of the plurality of sub-volumes, where the first planar data is acquired with the ultrasound imaging system in a second imaging mode that is different than the first imaging mode, wherein the second imaging mode is selected from the group consisting of B-mode, color Doppler, color M-mode, TVI, strain, and strain rate;
displaying a first reference image based on the first planar data on a display during the process of acquiring the first volumetric data;
displaying a first image based on the first volumetric data on the display;
an imaging mode that is one of colorflow and B-mode;
iteratively acquiring first planar data of a plane through the volume-of interest with the ultrasound imaging system in between acquiring each of the plurality of sub-volumes, where the first planar data is acquired with the ultrasound imaging system in a second imaging mode that is different than the first imaging mode, wherein the second imaging is the other of colorflow and B-mode;
displaying a first reference image based on the first planar data on a display during the process of acquiring the first volumetric data;
displaying a first image based on the first volumetric data on the display;
positioning a the probe based on the first image and the first reference image;
acquiring second volumetric data of the volume of interest with the ultrasound probe by acquiring a second plurality of sub-volumes with the ultrasound imaging system for multiple cardiac cycles after the first cardiac cycle, each of the second plurality of sub-volumes representing a different portion of the volume of interest, where the second volumetric data is acquired with the ultrasound imaging system in the second imaging mode;
iteratively acquiring second planar data of a second plane through the volume of interest with the probe in between said acquiring the second plurality of sub-volumes, where the second planar data is acquired with the ultrasound imaging system in the first imaging mode;
positioning the probe based on the first image and the first reference image;
acquiring second volumetric data of the volume of interest with the probe by acquiring a second plurality of sub-volumes with the ultrasound imaging system for multiple cardiac cycles after the first cardiac cycle, each of the second plurality of sub-volumes representing a different portion of the volume of interest, where the second volumetric data is acquired with the ultrasound imaging system in the second imaging mode;
iteratively acquiring second planar data of a second plane through the volume of interest with the probe in between said acquiring the second plurality of sub-volumes, where the second planar data is acquired with the ultrasound imaging system in the first imaging mode;
displaying a second reference image based on the second planar data on the display during the process of acquiring the second volumetric data; and
displaying a second image based on the second volumetric data on the display.

9. A method of ultrasound imaging comprising:
acquiring first volumetric data of a volume of interest with a probe that is a component of an ultrasound imaging system by acquiring a first plurality of sub-volumes with an ultrasound imaging system during first cardiac cycle, each of the first plurality of sub-volumes representing a different portion of the volume of interest, where the first volumetric data is acquired with the ultrasound imaging system in displaying a second reference image based on the second planar data on the display during the process of acquiring the second volumetric data; and
displaying a second image based on the second volumetric data on the display.

10. A method of ultrasound imaging comprising:
acquiring first volumetric data of a volume of interest with a probe that is a component of an ultrasound imaging system by acquiring a first plurality of sub-volumes with an ultrasound imaging system during first cardiac cycle, each of the first plurality of sub-volumes representing a different portion of the volume of interest, where the first volumetric data is acquired with the ultrasound imaging system in an imaging mode selected from group consisting of B-mode, color Doppler, color M-mode, TVI, strain, and strain rate;
iteratively acquiring first planar data of a plane through the volume-of interest with the ultrasound imaging system in between acquiring each of the plurality of sub-volumes, where the first planar data is acquired with the ultrasound imaging system in a second imaging mode that is different than the first imaging mode, wherein the second imaging mode is selected from the group consisting of B-mode, color Doppler, color M-mode, TVI, strain, and strain rate;
displaying a first reference image based on the first planar data on a display during the process of acquiring the first volumetric data;
displaying a first image based on the first volumetric data on the display, wherein the first image based on the first volumetric data is displayed at the same time as the first reference image;
positioning a the probe based on the first image and the first reference image;
acquiring second volumetric data of the volume of interest with the ultrasound probe by acquiring a second plurality of sub-volumes with the ultrasound imaging system for multiple cardiac cycles after the first cardiac cycle, each of the second plurality of sub-volumes representing a different portion of the volume of interest, where the second volumetric data is acquired with the ultrasound imaging system in the second imaging mode;
iteratively acquiring second planar data of a second plane through the volume of interest with the probe in between said acquiring the second plurality of sub-volumes, where the second planar data is acquired with the ultrasound imaging system in the first imaging mode;
displaying a second reference image based on the second planar data on the display during the process of acquiring the second volumetric data; and
displaying a second image based on the second volumetric data on the display.

11. A method of ultrasound imaging comprising:
acquiring first volumetric data of a volume of interest with a probe that is a component of an ultrasound imaging system by acquiring a first plurality of sub-volumes with an ultrasound imaging system during first cardiac cycle, each of the first plurality of sub-volumes representing a different portion of the volume of interest, where the first volumetric data is acquired with the ultrasound imaging system in an imaging mode selected from group consisting of B-mode, color Doppler, color M-mode, TVI, strain, and strain rate;
iteratively acquiring first planar data of a plane through the volume-of interest with the ultrasound imaging system in between acquiring each of the plurality of sub-volumes, where the first planar data is acquired with the ultrasound imaging system in a second imaging mode that is different than the first imaging mode, wherein the second imaging mode is selected from the group consisting of B-mode, color Doppler, color M-mode, TVI, strain, and strain rate;
displaying a first reference image based on the first planar data on a display during the process of acquiring the first volumetric data;
displaying a first image based on the first volumetric data on the display;
positioning a the probe based on the first image and the first reference image;
acquiring second volumetric data of the volume of interest with the ultrasound probe by acquiring a second plurality of sub-volumes with the ultrasound imaging system for multiple cardiac cycles after the first cardiac cycle, each of the second plurality of sub-volumes representing a different portion of the volume of interest, where the second volumetric data is acquired with the ultrasound imaging system in the second imaging mode;
iteratively acquiring second planar data of a second plane through the volume of interest with the probe in between said acquiring the second plurality of sub-volumes, where the second planar data is acquired with the ultrasound imaging system in the first imaging mode;
displaying a second reference image based on the second planar data on the display during the process of acquiring the second volumetric data; and
displaying a second image based on the second volumetric data on the display; and
acquiring third planar data of the plane through the volume of interest with the ultrasound imaging system in between said acquiring each of the second plurality of sub-volumes, where the third planar data is acquired with the ultrasound imaging system in an imaging mode that is different than the second ultrasound imaging mode.

12. The method of claim 11, further comprising displaying a third reference image based on the third planar data at the same time as both the second reference image and the second image based on the second volumetric data, wherein the third reference image is displayed separately from the second reference image.

* * * * *